United States Patent
Chabanis et al.

(10) Patent No.: US 7,456,969 B2
(45) Date of Patent: Nov. 25, 2008

(54) DEVICE AND METHOD FOR MONITORING THE OXYGEN CONCENTRATION IN AN AIRCRAFT TANK

(75) Inventors: Gilles Chabanis, Versailles (FR); Maximilian Fleischer, Hohenkirchen (DE); Philippe Mangon, Elancourt (FR); Hans Meixner, Haar (DE); Rainer Strzoda, Munich (DE)

(73) Assignee: Siemens Schweiz AG, Zurich (CH)

( * ) Notice: Subject to any disclaimer, the term of this patent is extended or adjusted under 35 U.S.C. 154(b) by 283 days.

(21) Appl. No.: 10/559,261

(22) PCT Filed: Jun. 8, 2004

(86) PCT No.: PCT/EP2004/051062

§ 371 (c)(1),
(2), (4) Date: Dec. 2, 2005

(87) PCT Pub. No.: WO2004/113169

PCT Pub. Date: Dec. 29, 2004

(65) Prior Publication Data
US 2006/0163483 A1 Jul. 27, 2006

(30) Foreign Application Priority Data
Jun. 16, 2003 (DE) ................. 103 27 060

(51) Int. Cl.
*G01N 21/00* (2006.01)
(52) U.S. Cl. ............. 356/437; 250/343; 250/341.4
(58) Field of Classification Search ......... 356/432–440, 356/409, 307; 250/343, 345, 341.4
See application file for complete search history.

(56) References Cited

U.S. PATENT DOCUMENTS

| | | | | |
|---|---|---|---|---|
| 4,934,816 A | * | 6/1990 | Silver et al. | 356/409 |
| 5,047,639 A | | 9/1991 | Wong | |
| 5,317,156 A | * | 5/1994 | Cooper et al. | 250/345 |
| 5,572,031 A | * | 11/1996 | Cooper et al. | 250/343 |
| 5,625,189 A | * | 4/1997 | McCaul et al. | 250/343 |
| 5,650,845 A | * | 7/1997 | Kebabian | 356/307 |
| 6,136,267 A | | 10/2000 | Bergman | |
| 6,493,086 B1 | * | 12/2002 | McAndrew et al. | 356/437 |
| 6,912,480 B2 | * | 6/2005 | Black | 702/183 |

FOREIGN PATENT DOCUMENTS

| EP | 0 874 233 | 10/1998 |
|---|---|---|
| EP | 0 984 267 | 3/2000 |

* cited by examiner

*Primary Examiner*—Hoa Q Pham
(74) *Attorney, Agent, or Firm*—Young & Thompson

(57) ABSTRACT

The invention relates to a device for monitoring the oxygen concentration in an aircraft tank. The device includes an absorption measuring section equipped with a laser or laser diode (6), a photodiode (7), a temperature sensor (8) and a reflector (5) for carrying out laser spectroscopy on a gas volume to be measured inside the tank. The conducting components of the device are positioned outside the tank and its reflector (5) is positioned in the tank in the gas volume to be measured, the components and reflector being optically coupled by a window (3) that is situated in the tank wall (2). The absorption measuring section is mainly located in the chamber containing the gas to be measured.

20 Claims, 1 Drawing Sheet

DEVICE AND METHOD FOR MONITORING THE OXYGEN CONCENTRATION IN AN AIRCRAFT TANK

Figure 1:
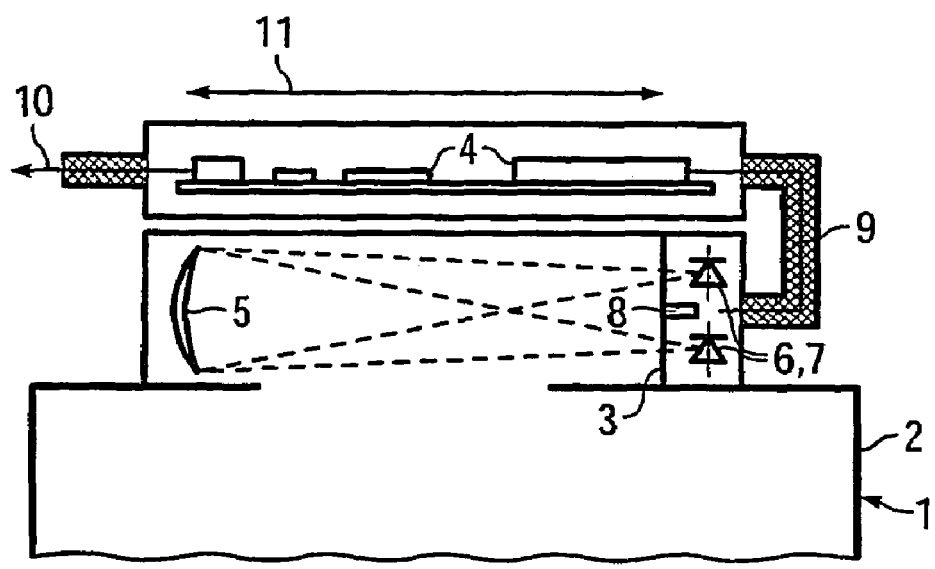

The invention relates to a device and a method for detecting and monitoring the oxygen concentration in an aircraft tank using laser spectroscopy for which an absorption measuring section is implemented in a gas volume to be measured inside the tank. With the known laser spectroscopy method, ignition thresholds of gas mixtures in the aircraft tank are monitored, the target gas of the measurement being oxygen.

In the aviation sector in recent decades a number of aircraft crashes are known which, according to the latest findings, were caused by explosions in aircraft tanks. A particularly stark incident was an aircraft crash in which an explosion occurred shortly after takeoff in New York in July 1996. On that occasion a fuel tank exploded and led to the crash of the aircraft. The exact cause for the igniting of the explosion could not be determined in detail. Following this incident, however, the discussion on how to prevent such incidents intensified considerably. The American Federal Aviation Authority (FAA) initiated a program in which various approaches to assure reliable operation of aircraft tanks are examined. One possibility consists in preventing the formation of an ignitable air/fuel mixture in the tank by lowering the oxygen component. This is described for example in literature reference [1], where there is also carried on board an aircraft a system which generates the nitrogen-enriched air. The tanks are filled with this air until the oxygen concentration falls below the lower ignition threshold. Depending on operating conditions, this threshold lies between 11.5 and 12% oxygen by volume. Literature reference [2] is relevant in this regard. In order to check the effectiveness of this measure the oxygen concentration in the tanks must be continuously monitored. The difficulty in performing the measurement lies in the fact that in larger aircraft there are a number of tanks and each of these is subdivided in order to prevent an uncontrolled flow of fuel. This results in a large number of individual gas-filled cavities which make it difficult to achieve homogeneous flushing with inert gas. This leads to the necessity of measuring the oxygen content at a plurality of points.

Systems for inerting an aircraft tank with nitrogen-enriched air have not been used routinely in the past. In experiments with aircraft tanks a central oxygen monitor has been used to which the air to be investigated is supplied from the individual tanks via a piping system. In this arrangement the individual measurement points are cyclically polled in succession. On this point, see literature reference [3]. With this system, conveying the gas to be measured requires a considerable technical outlay. Since an additional power system for potentially explosive gas mixtures is required, this constitutes an additional danger source.

There are numerous methods for measuring the oxygen concentration. The most well-known methods are associated with an electrochemical cell, pump probes with solid electrolytes (lambda probe), methods which exploit the paramagnetism of oxygen as a measurement effect, fluorescence quenching or optical absorption spectroscopy.

Most of these methods are little suited to use in or on the aircraft tank, since heavy demands are imposed here on an appropriate sensor. A sensor in this environment should, for example, have a life expectancy of well over 10 years.

Furthermore a calibration of the concentration having long-term stability is necessary. The method must be able to check itself in order to preclude erroneous measurements. The operating temperature should lie in the range from −55° C. to +85° C. The sensor must withstand fluctuations in air pressure in the range from 250 to 1100 mbar. The humidity of the air in the measurement region lies between 0 and 100% relative humidity.

The electrochemical cells used in the tests have certain serious disadvantages for the planned application. For example, limited lifetimes of approx. 2 years result, necessitating costly replacement at regular intervals. Since humidity is required for the operation of the electrochemical cell, the cell can quickly dry out in dry air, as is the desired aim in aircraft. This leads to a shortening of the lifespan. In addition, operation at low temperatures is not possible because the electrolyte freezes.

Pump probes with solid electrolyte are disqualified because they have to be heated up to several 100° C. in order to operate and consequently constitute an ignition source for the air/fuel mixture.

Paramagnetic methods use a complicated mechanical measuring system with a scale which is susceptible to vibrations and accelerations such as occur in aircraft.

Efforts are currently being made to develop sensors operating according to the fluorescence quenching principle for the targeted application. With this approach, short-wave light pulses are brought by means of an optical wave guide into an area of the fiber which is coated with a special fluorescing substance. The fluorescence intensity and the decay time of the fluorescence are dependent on the oxygen concentration in the environment. A disadvantage with this method is the absence of a self-check capability. The correlation of the oxygen concentration with the measurable variable depends on the long-term chemical stability of the fluorescence layer with respect to any environmental influences occurring.

The object of the invention is to provide a device and a method by means of which the build-up of ignitable gas mixtures inside an aircraft tank can be detected.

This object is achieved by the respective feature combination of claims 1 and 10 respectively. Advantageous embodiments can be derived from the respective dependent claims.

The invention is based on the knowledge that all in all laser absorption spectroscopy meets the requirements for a sensor for detecting oxygen in an aircraft tank, the laser absorption spectroscopy being used in the visible and infrared wavelength range. Evaluated in particular are individual, in each case selected, absorption lines of the oxygen molecules in the range between 758 and 766 nm.

Laser absorption spectroscopy is a method known per se. Lasers or laser diodes which emit in monochrome in the static operating state are used. Use is made here of the wavelength tunability, for example by variation of the operating temperature. This enables a wavelength interval which is set in place of a selected absorption line in the spectrum of the target gas, in this case oxygen, to be scanned. The laser light irradiates a selectively positioned gas absorption section in which the oxygen is located if it is present in the tank. If oxygen is present, a wavelength-dependent attenuation of the penetrating light will occur. The attenuation always correlates with the concentration of the gas to be measured. A photodetector records the spectrum, which will be conditioned in a following signal processing electronics circuit and evaluated by means of appropriate software on a processor. Usable methods for the purpose of evaluation in laser spectroscopy are either direct absorption measurement, a derivative method or high-frequency modulation methods such as, for example, the heterodyne method, as described in the literature references [4] and [5].

The absorption measurement section is positioned on the tank of an aircraft in such a way that all components of the sensor that are connected by means of electrical leads are placed outside the tank or outside the tank wall. Only a retainer with a back-reflecting element present at the end projects into the interior of the tank. The entire arrangement is mounted in the upper area of a tank, in particular at a raised position at which the tank has, for example, a bulge. This positioning is associated with the fact that the measurement is taken in the gas phase. The oxygen sensor should ideally not be immersed in fuel or, as the case may, should be able to take the measurement as quickly as possible in a gas volume in which gases accumulate inside an aircraft tank. As a result the transmitting and receiving elements as well as usually also a temperature sensor are thus located outside the tank wall, a feed-through opening in the tank wall is terminated by a window that is transparent to the light wavelengths used during operation, and retainer and reflector project into the tank such that an absorption measurement section is represented inside the tank. The reflector can advantageously be a retroreflector. Further advantages are achieved by means of a concave mirror.

The ignitable mixtures are monitored by means of the detection of oxygen with the additional measurement of the oxygen concentration. Typically, a lower ignition threshold of a mixture composed of oxygen and the possible vapors of the fuel will be monitored by measurement of the oxygen concentration.

Exemplary embodiments are described below with reference to schematic figures which do not limit the scope of the invention.

Figure 2:
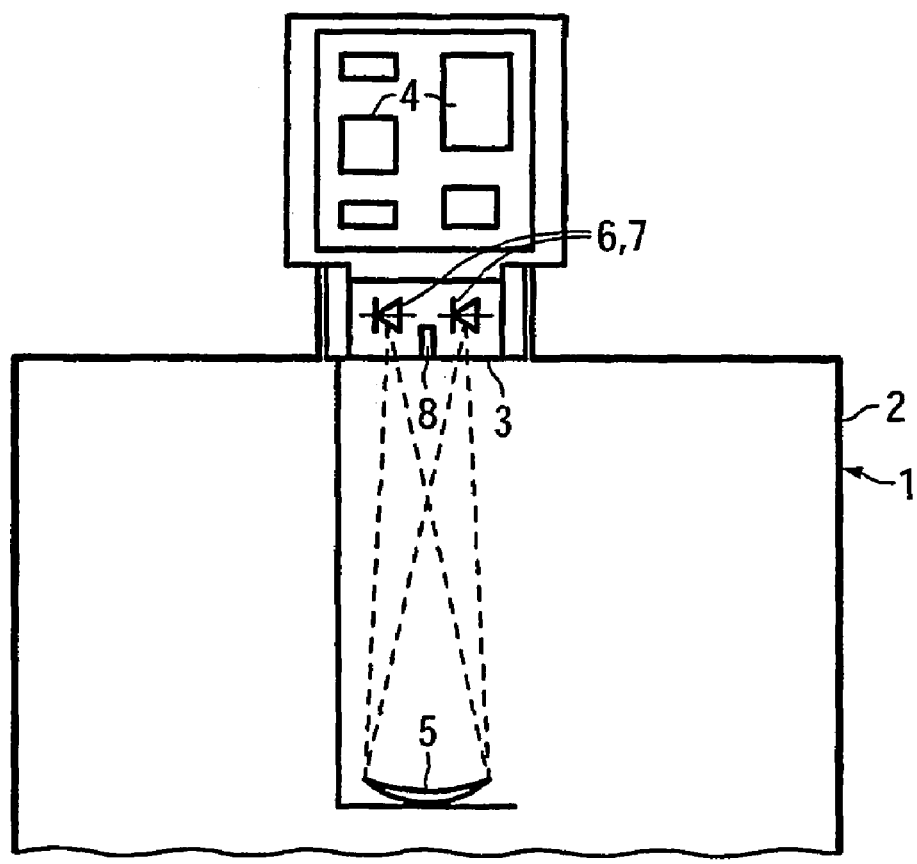

FIG. 1 shows an exemplary embodiment of the oxygen monitor, mounted at the top of an aircraft tank, FIG. 2 shows an alternative embodiment of the oxygen monitor which is mounted in the tank wall by means of a single-hole assembly with thread and seal.

FIG. 1 shows an exemplary embodiment of a measuring probe mounted in the upper part of the aircraft tank. Laser and photodetector are located outside the tank interior. Only the optical laser beam passes through a window 3 into the interior of the tank 1, where the oxygen absorption is to be measured in a measurement gas volume. This form of construction avoids the need to route additional electrical leads into the tank, which electrical leads basically represent a potential explosion risk. In the exemplary embodiment according to FIG. 1 a concave mirror reflects the light and focuses it onto the photodetector, the photodiode 7. The reflector 5 can also be represented as a simply diffusely reflecting surface, albeit with a collecting optical system being required in the beam path for conditioning the receive signal.

FIG. 2 shows an alternative embodiment relative to FIG. 1. The advantage of this arrangement lies in the simple assembly. The monitor is screwed into a tapped hole in the tank wall. The sensor will ideally be mounted at the most raised point of the tank so as to minimize the probability that fuel will intrude into the beam path. Provided the beam path is not constantly blocked by fuel, a spectral measurement will be possible since it takes only a few milliseconds to record a spectrum. Spectra which are partially or totally prejudiced by fuel in the beam path of the absorption measurement section can be easily distinguished from undisturbed spectra and so can be filtered out for the purposes of the measurement.

Since the method has a high dynamic range for the optical receive signal (see literature reference [6]), a misting up of the window 3 or the reflector 5 can also be tolerated within wide limits. As the spectral measurement always yields the entire absorption line, in particular also the areas in which no or only little absorption occurs, such as, for example, an area near to an absorption line, the measurement background is known and a wavelength-independent change in the transmissions of the measurement cell does not interfere with the concentration measurement. The concentration of the gas is proportional to the ratio of the minimum transmission in the center of the absorption line to the transmission near to the line.

Furthermore the narrow spectral line width of the laser emission, which is typically less than 1% of the half-value width of the absorption line, permits a spectrum to be recorded without spectral broadening caused by the measuring instrument. The measured spectrum can be compared directly with a calculated spectrum, given knowledge of the molecule parameters such as the transition frequency, integrated line strength, pressure distribution coefficient and energy of the initial state as well as length of the absorption path, temperature and pressure. Then, the only free parameter is the gas concentration. Thus, no device parameters are included in the calculation. This makes the method into a reference method, which means it is predestined for the desired application, where what it essentially comes down to is the long-term stability of the concentration calibration.

The parameters of the laser diode which are included in the measurement are the curvature of the laser characteristic curve and the correlation between the laser current and the emission wavelength. The curvature of the laser characteristic curve is assumed to be parabolic. A change in the curvature is taken into account in the evaluation and therefore does not influence the measurement result. The change in the correlation between laser current and emission wavelength can be recalibrated at any time by measuring the oxygen spectrum at different temperatures.

For the purposes of self-adjustment it should be noted that in the normal case a small correction has to be made in the event that the measured position of the absorption line does not tally with the stored position. In this case the instrumental wavelength scale is shifted until the two positions of the absorption lines match once more. If the discrepancy is greater, a larger area of the spectrum must be measured (at different temperatures) in which a number of absorption lines occur. From the known intensity ratio of the different lines, the measured spectrum can then be uniquely assigned to the stored spectrum with regard to the wavelength scale.

Provided a residual amount of oxygen is still present in the tank, an oxygen absorption can always be identified with certainty. This means that the system can check itself. Provided the absorption is measured, it is ensured that the laser wavelength is correct and the complete evaluation electronics and software are operating correctly. If no oxygen is to be expected in the measurement cell, beam splitting can be used to create a reference path in which a reference cell containing oxygen is disposed. A photodetector in the reference branch then records the spectrum. The evaluation takes place as in the present case. No moving parts are required. There is therefore also no mechanical wear and tear and no influencing of the results by vibrations and accelerations.

The laser spectroscopy method for detecting oxygen generally meets the requirements for use on an aircraft tank. Certain features stand out in particular here. A very important feature is the self-check, so that it can automatically be determined at any time whether the current measurement is correct or not. This is based on the knowledge that a predetermined signature, that is to say an absorption spectrum of the oxygen line, must be present at all times so as to provide sufficient features for an unequivocal identification of the measurement gas spectrum.

In detail, FIG. 1 shows a tank 1 which is partially opened up and bordered by a tank wall 2. Relative to the measurement window 3, the parts of the absorption measurement section that are placed inside the tank volume, the reflector 5 and a retainer (not shown), can be clearly separated from the components of the absorption measurement section which are positioned outside the tank volume and have an electrical power supply. In this case the window 3 becomes a part of the tank wall 2. A sensor electronics circuit 4 which is also mounted externally and is likewise insulated from the tank is connected to the absorption measurement section via electrical connections 9. By means of the transmission 10, conditioned measurement signals can be transmitted to the exterior. The adequate length 11 of the absorption measurement section is approximately 2×5 cm, the double passage of the light beams being taken into account.

FIG. 2 shows an alternative embodiment of the oxygen monitor with a design which allows the sensor to be installed vertically with respect to the tank wall 2. In this arrangement the transmitter is guided through the tank wall 2 vertically with respect thereto and clamped or, as the case may be, screwed in place. Just as in FIG. 1, the reflector 5 together with the electrically connected components of the laser diode 6, the photodiode 7 and the temperature sensor 8 represents the absorption measurement section, with the window 3 constituting a separating line between components located inside and components located outside the tank. In this case the window 3 is once again a replacement for the tank wall 2.

REFERENCES

[1] FAA Report No.: DOT/FAA/AR-01/6, Inerting of a vented aircraft fuel tank test article with nitrogen-enriched air, M. Barns, W. M. Cavage, April 2001
[2] FAA Report No.: FAA-RD-71-42, Inerted fuel tank oxygen concentration requirements, S. V. Zinn, Jr., August 1971
[3] FAA Report No.: DOT/FAA/AR-01/63, Ground and flight testing of Boeing 737 center wing fuel tank inerted with nitrogen-enriched air, M. Barns, W. M. Cavage, August 2001
[4] IPM-Forschungsberichte 24-4-92, R. Grisar, Quantitative Gasanalyse mit abstimmbaren IR-Diodenlasern, 1992 (IPM research reports, "*Quantitative gas analysis using tunable IR diode lasers*")
[5] Patent specification U.S. Pat. No. 5,625,189, McCaul et al.
[6] Takaya Iseki, Hideo Tai, Kiyoshi Kimura, A portable remote methane sensor using a tunable diode laser, Meas. Sci. Technol., 11, 2000, 594-602

The invention claimed is:

1. A device for monitoring the oxygen concentration in an aircraft tank, having an absorption measurement section with laser or laser diode (6) and photodiode (7) for laser spectroscopy on a gas volume to be measured inside the tank, wherein the current-carrying components of said device are positioned outside the tank chamber and the absorption section of said device is positioned in the gas volume to be measured essentially inside the tank chamber, and are optically coupled to one another via at least one window (3) located in the tank wall (2), and
 the oxygen concentration is determined by a measured spectrum of said measurement section being compared directly with a calculated spectrum of given knowledge of molecule parameters including transition frequency, integrated line strength, pressure distribution coefficient, energy of an initial state, length of an absorption path, temperature, and pressure.

2. The device as claimed in claim 1,
 wherein the i) laser or laser diode (6) and ii) photodiode (7) are positioned jointly at one end of the absorption measurement section and measurement beams are reflected at the opposite end by means of a reflector (5).

3. The device as claimed in claim 2,
 wherein the reflector (5) is embodied as a retroreflector or as a diffusely reflecting surface, with a collecting optical system being present directly in front of the photodetector (7).

4. The device as claimed in claim 2,
 wherein the reflector (5) is embodied as a concave mirror.

5. The device as claimed in claim 2,
 wherein the absorption measurement section for laser spectroscopy is positioned and fixed in a vertical feed-through opening in the tank wall (2).

6. The device as claimed in claim 5, wherein the absorption measurement section for laser spectroscopy is screwed into a tapped hole in the tank wall (2).

7. The device as claimed in claim 2,
 wherein a temperature sensor (8) is present in the area of the laser or the laser diode (6) for the purpose of stabilizing the temperature of the laser or the laser diode (6).

8. The device as claimed in claim 1,
 wherein a temperature sensor (8) is present in the area of the laser or the laser diode (6) for the purpose of stabilizing the temperature of the i) laser or the laser diode (6).

9. The device as claimed in claim 8,
 wherein the reflector (5) is embodied as a retroreflector or as a diffusely reflecting surface, with a collecting optical system being present directly in front of the photodetector (7).

10. The device as claimed in claim 1,
 wherein absorption lines for laser spectroscopy for detecting oxygen are selected in the wavelength range between 758 and 766 nm.

11. The device as claimed in claim 10,
 wherein the reflector (5) is embodied as a retroreflector or as a diffusely reflecting surface, with a collecting optical system being present directly in front of the photodetector (7).

12. The device as claimed claim 1,
 wherein the absorption measurement section for laser spectroscopy is positioned in the upper area of an aircraft tank (1).

13. The device as claimed in claim 1,
 wherein the tank wall (2) has a bulge or a lead connection separated from the essential tank volume by a choke point, with the absorption measurement section being represented at the end of the bulge or lead facing away from the tank in a measurement gas volume that is connected to the tank volume.

14. The device as claimed in claim 1,
 wherein a reference path is present outside the tank (1) to provide a reference cell containing oxygen after the splitting of a measurement beam.

15. A method for detecting oxygen in a gas volume to be measured in aircraft tanks (1) with laser spectroscopy, comprising measuring the presence and concentration of oxygen with laser spectroscopy with the measured device according to claim 1.

16. The method as claimed in claim 15, further comprising monitoring ignition thresholds of ignitable mixtures based on the detection of the concentration of oxygen.

17. The method as claimed in claim 16, further comprising performing a self-adjustment with regard to the line in the oxygen spectrum when a selected partial area of the oxygen spectrum is compared with the spectrum of a measurement.

18. The method as claimed in claim 15, further comprising performing a self-adjustment with regard to the line in the oxygen spectrum when a selected partial area of the oxygen spectrum is compared with the spectrum of a current measurement.

19. The method as claimed in claim 15, further comprising performing a self-adjustment with regard to the line in the oxygen spectrum when a selected partial area of the oxygen spectrum is compared with the spectrum of a measurement.

20. A device for monitoring the oxygen concentration in an aircraft tank, said device, comprising:
   an absorbent measurement section positioned on said aircraft tank to monitor the oxygen concentration inside an upper region of said aircraft tank with a gaseous region over a remaining fuel present, said absorbent measurement section comprising
   i) a laser or laser diode (6) for laser spectroscopy on a gas volume to be measured inside the tank,
   ii) a photodiode (7) for laser spectroscopy on a gas volume to be measured inside the tank,
   wherein the laser or laser diode and photodiode are positioned on the outside of said aircraft tank and optically coupled to one another via at least one window (3) located in the tank wall (2) so that the laser or laser diode irradiates with light a selectively positioned gas volume in said aircraft tank so that the concentration of oxygen, if present, can be measured with said photodiode, and
   the oxygen concentration is determined by a measured spectrum of said measurement section being compared directly with a calculated spectrum of given knowledge of molecule parameters including transition frequency, integrated line strength, pressure distribution coefficient, energy of an initial state, length of an absorption path, temperature, and pressure.

* * * * *